(12) United States Patent
Parkin et al.

(10) Patent No.: US 6,432,113 B1
(45) Date of Patent: Aug. 13, 2002

(54) SKIN ABRASION DEVICE

(76) Inventors: Roger C. Parkin, 15 Springton Point Dr., Newtown Sq., PA (US) 19073; George Maguire, 104 Campbell Dr., Conshohocken, PA (US) 19428

( * ) Notice: Subject to any disclaimer, the term of this patent is extended or adjusted under 35 U.S.C. 154(b) by 0 days.

(21) Appl. No.: 09/255,954

(22) Filed: Feb. 23, 1999

(51) Int. Cl.$^7$ .............................................. A61B 17/50
(52) U.S. Cl. ........................................ 606/131; 604/22
(58) Field of Search ................................ 606/131, 159, 606/161, 162; 433/88, 136; 604/22; 601/155; 55/476, 467, 482; D23/364–365; 751/322

(56) References Cited

U.S. PATENT DOCUMENTS

| | | | |
|---|---|---|---|
| 3,974,833 A | 8/1976 | Durden, III | 128/275.1 |
| 5,037,432 A | 8/1991 | Molinari | 606/131 |
| 5,100,412 A | * 3/1992 | Rosso | 606/131 |
| 5,207,234 A | * 5/1993 | Rosso | 606/131 |
| 5,460,604 A | 10/1995 | Arnett et al. | 604/35 |
| 5,470,305 A | 11/1995 | Arnett et al. | 601/161 |
| 5,562,643 A | 10/1996 | Johnson | 604/290 |
| 5,674,235 A | 10/1997 | Parisi | 606/169 |
| 5,730,769 A | * 3/1998 | Dungs et al. | 55/385 |
| 5,807,386 A | 9/1998 | Slatkine et al. | 606/9 |
| 5,954,730 A | * 9/1999 | Bernabei | 606/131 |
| 5,971,999 A | * 10/1999 | Naldoni | 606/131 |
| 6,036,684 A | 3/2000 | Tankovich et al. | 606/9 |
| 6,039,745 A | 3/2000 | Di Fiore et al. | 606/131 |

FOREIGN PATENT DOCUMENTS

| | | |
|---|---|---|
| EP | 0564392 | 10/1993 |
| EP | 0324448 | 3/1995 |
| EP | 0806184 | 11/1997 |
| FR | 2712172 | 5/1995 |
| WO | 9700050 | 1/1997 |
| WO | 9711650 | 4/1997 |
| WO | 9923951 | 5/1999 |
| WO | 0002602 | 1/2000 |

OTHER PUBLICATIONS

Ravi Pachigolla, M.D., "Dermabrasion And Chemical Peels", Grand Rounds of the UTMB Department of Otolaryngology, Jan. 8, 1997.
Hard copy printout of Internet www pages from Permark web site, 5 pages, URL is http://www.permark.com, download date of May 19, 2000.
Hard copy printout of Internet www pages from Dermabraders web site, 5 pages, URL is http://www.justinscientific.com, download date of May 23, 2000.
Hard copy printout of Internet www pages from Derma Genesis web site, 3 pages, URL is http://www.dermagenesis.com, download date of May 19, 2000.

* cited by examiner

Primary Examiner—David O. Reip
Assistant Examiner—Julian W. Woo
(74) Attorney, Agent, or Firm—Ostrolenk, Faber, Gerb & Soffen, LLP (57) ABSTRACT

A novel handpiece and system for abrasion of skin is disclosed. A short handpiece with a threadably movable tip is used. The opening in the tip is centered on the handpiece axis and a small diameter particle input channel and diameter larger output channel are both offset from the handpiece axis. A vacuum control opening is formed in the tip for easy control by the operator. Abrasive particles and removed tissue are applied to the interior of a cylindrical filter supported within a support can. The annular area between the can and filter is connected through a secondary emergency filter to a vacuum pump. The cylindrical filter can be a flexible filter bag. A large source of abrasive particles is coupled to the handpiece inlet and the filter is coupled to the handpiece outlet.

35 Claims, 5 Drawing Sheets

SKIN ABRASION DEVICE

FIELD OF THE INVENTION

This invention relates to the removal of surface portions of dead or living tissue, sometimes termed microdermal abrasion and more specifically relates to an improved apparatus and process for the abrasion of surface portions of human tissue by the controlled flow of abrasive particles.

BACKGROUND OF THE INVENTION

Apparatus for the microdermal abrasion of the surface of tissue (living or dead) is well known. In these processes, a stream of abrasive particles such as sand is applied to the surface of the tissue or skin through an opening in a hand held tool (termed a handpiece) which is sealed against the skin. The tool and the particle stream is controllably scanned over the area to be abraded. The abrading particles and the removed tissue are then collected by vacuum in the handpiece and are passed through and collected by a filter to prevent the escape of the abraded tissue and sand into the vacuum pump and ambient atmosphere.

The handpiece has taken many forms in the past but usually provides a first passage for conducting abrasive particles from a reservoir to the area to be treated and a second parallel channel for conducting the particles and abraded skin away from the area treated and into a disposal vessel.

A typical prior art apparatus is shown in U.S. Pat. No. 5,037,432. The hand-held head of this patent is a long tubular structure having an off-center hole which permits the application of an abrasive particle jet to an area to be treated, and the subsequent removal of the particles and abraded skin. The off-center outlet hole is arranged to be on the same axis as the input abrasive particle jet which then reaches the area to be treated at a 45° angle. The outlet jet channel facing the opening has a nozzle restriction. The abraded skin and used particles are then withdrawn through a parallel return vacuum channel which is connected to a vacuum pump through a filter.

The above described hand held tool has a number of drawbacks. Thus, because it is relatively long (longer than about 5 inches) it is difficult to manipulate easily over a curved surface area to be abraded, for example, the surface of a human face. Further, the vacuum pressure within the hand tool is not easily changed by the operator when a weaker or more forceful jet of abrasive particles is desired at particular locations on the surface area being abraded. Further, the handpiece is subject to clogging at the restricted outlet nozzle, requiring the operator frequently to stop the treatment and clear the nozzle.

The above described handpiece is provided with a removable and disposable tip or bell section which contains the output hole. Thus, the tip can be removed and disposed of and replaced by a new tip after the treatment of each individual. The tip is normally press-fit onto the body of the handpiece and is tightly sealed thereto to prevent accidental escape of abraded skin and loss of vacuum. Therefore, the tip is very difficult to remove and replace.

It would be very desirable to provide a handpiece for abrasion of living tissue which avoids the above problems.

The abrasive particles and tissue which are removed in prior art devices are collected in a filter placed between the handpiece outlet channel and the vacuum pump. Such a filtration system is shown in U.S. Pat. No. 5,100,412 and 5,207,234 in the name of Rosso. The filter shown therein is an inverted cup at the outlet opening of a waste receiving chamber. The outlet opening is connected to the vacuum pump line and contaminated particles and debris flow from the cup exterior toward its interior thus building up on the cup exterior. This filter tends to become quickly clogged and becomes more and more imperious to the flow of air therethrough. Consequently, the system must be frequently turned off and the filter must be cleaned sometimes during and frequently after each use.

It would be very desirable to provide a filtration system which does not require frequent cleaning or emptying.

SUMMARY OF THE INVENTION

In accordance with the invention a novel apparatus and process is provided which avoids the problems with prior art devices as stated above, and which provides added improved operation as well.

In accordance with a first feature of the invention, a novel filtration system is provided in which a large area cylindrical filter is disposed coaxially within a large volume container with an annular air outlet chamber defined between the cylindrical filter and the container. The annular outlet channel is connected to the vacuum pump of the system.

In operation, abrasion particles and skin are conveyed from the outlet channel of the hand held instrument to the interior of the cylindrical filter and are then entrapped within the large surface area interior of the filter. Filtered air then passes through the filter and into the annular low pressure area surrounding the filter and then into the vacuum pump. Because of the large area of the filter, it need not be replaced frequently and will commonly not require replacement until after about 50 uses (or 50 patient treatments).

A back-up emergency filter is coupled between the annular filter volume and vacuum pump to prevent the flow of abrasion particles to the pump in the event of a failure or accidental bypass of the main filter.

The novel cylindrical filter may be mounted between top and bottom flexible disks or flanges which have a larger diameter than the cylindrical filter to permit the easy and rapid replacement of a new filter assembly after a given time or number of operations. The used sand and removed tissue will be trapped within the filter and between the gaskets during this operation. Note that the gaskets may have connection nipples or simple connection openings for input and output conduits which enter the filter interior and annular chamber respectively.

As an alternative to the above cylindrical filter which is rigid, it is also possible to employ a removable paper bag type of filter which is clamped around the inlet conduit, providing similar benefits to those described above at lower cost.

A novel hand-held head or handpiece is also provided with a novel modified design from that of the prior art.

As a first feature of the novel handpiece a screw-on tip of clear plastic is used which makes threaded engagement with the body of the tool. Thus the tip is easily removed from and replaced on the handpiece body after a single use. The tip is hemispherical in shape and has a sand-blast opening on the central axis. Sand input and output channels in the body extend parallel to its central axis and the axis of the tip and are displaced toward opposite sides of the central axis. Thus, the opening in the tip is on the central axis of the tool body but is displaced from the input and output channels. The sand will then sweep past the opening (and skin adjacent thereto) in its travel within the tip to abrade the skin.

Moreover, the diameter of the sand input channel to the tip interior is relatively smaller than the output vacuum channel (for example, 1/16 inch versus 1/8 inch respectively). This enables the quicker and easier withdrawal of used sand and skin particles from the interior vacuum chamber formed between the end of the body and the tip and aids in prevention of leakage of sand from the skin area being treated if the tip is removed from the area being treated. Note that in use, the hole in the tip is sealed against the skin area to preserve the vacuum and sand flow within the tip.

As a further feature of the novel handpiece, the entire body is shortened to a length less than about 3 inches. This makes it much easier to manipulate the tip over the surface being treated.

As a still further feature of the new handpiece, a small opening is provided in the side of the tip which can be easily covered by the finger of the operator. Thus, the vacuum pressure within the tip can be immediately changed by the operator without having to reach for the main pressure control at the main housing to which the handpiece is attached. It should be noted that this opening can also be placed in the handpiece body and can communicate with either the said inlet outlet channel and still accomplish the stated function.

As a still further feature of the handpiece, the end of the channel carrying sand to the tip is not restricted by a nozzle, but is of the same diameter as the input channel or even flared out to a larger diameter to prevent clogging of the input channel. The flare may also be used at the end of the output channel adjacent the tip. It has been found that the elimination of the nozzle does not otherwise affect the operation of the system.

As a further feature of the present invention, a novel large volume particle supply reservoir is provided in which, for example, a five pound supply of sand, for example, irregularly shaped aluminum oxide particles of a maximum dimension less than about 120 microns and with sharp irregular edges. A nipple at the bottom of the container is connected to an outlet tube, which in turn is coupled to a particle flow control valve which permits air flow into the conduit to carry the sand around the system with a controlled mass flow. The container can be easily replaced or replenished.

DETAILED DESCRIPTION OF THE INVENTION

Figure 1:
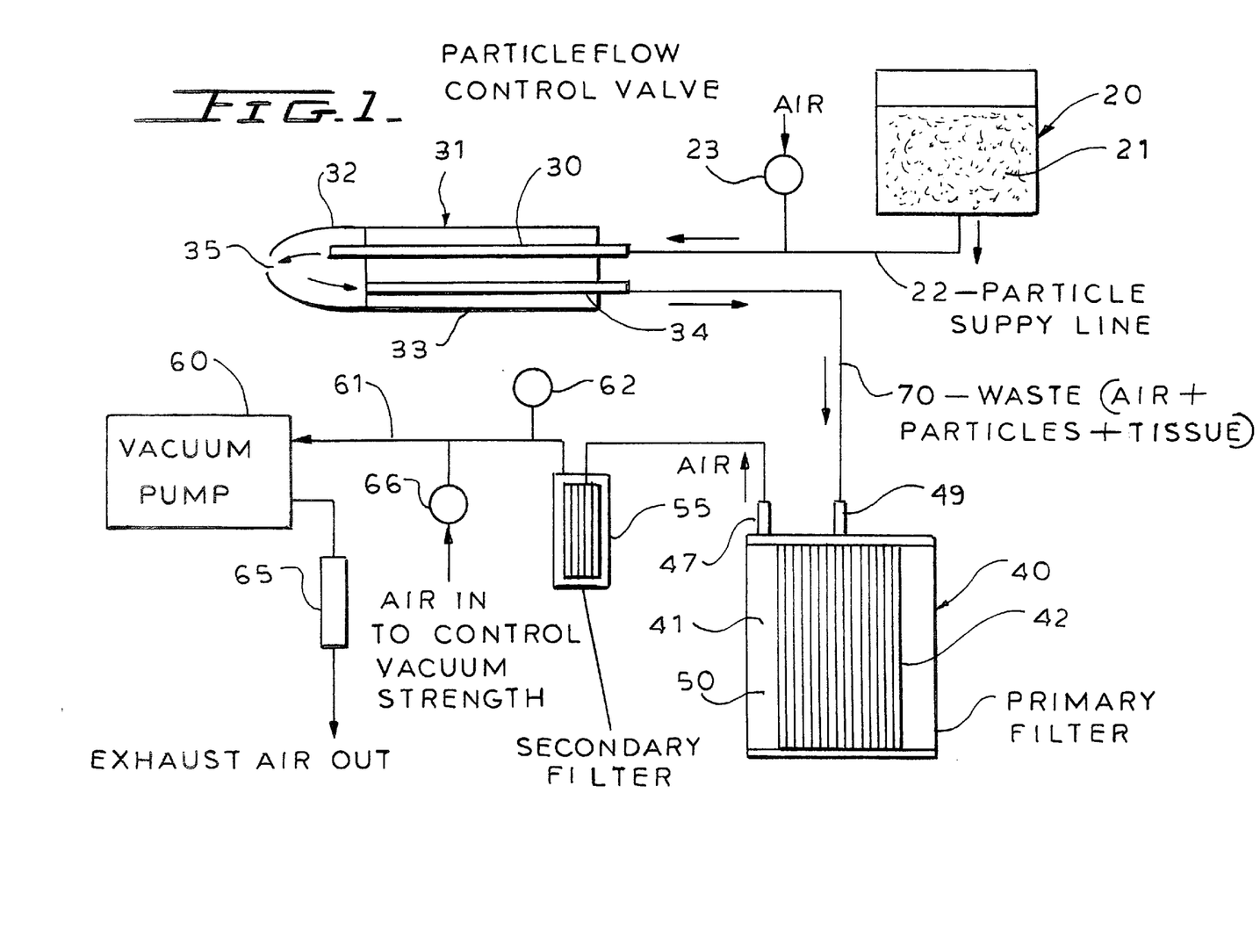
FIG. 1 is a schematic diagram of the novel system of the invention.

Referring first to FIG. 1, there is shown a supply container 20, which can, for example, contain about 5 pounds of a suitable abrasive sand 21, for example, aluminum oxide particles with very sharp edges and a non-critical maximum dimension of about 120 microns. An output particle supply line 22 which may be a plastic conduit of about 1/4 inch O.D. is connected to a suitable connection nipple (not shown) on the bottom of can 20. A particle flow control valve 23 is provided to control the air flow from atmosphere into supply line 22 to move abrasive particles in the input conduit 30 of handpiece 31; moving more sand when the valve is closed.

Handpiece 31 further contains a hemispherical shaped tip 32 which is removably connected to body 33. The body 33 contains input channel 30 and output channel 34 which will be later described in detail. Channel 30 conventionally has a diameter of about 1/8 inch and channel 34 is conventionally about 1 inch in diameter.

Removable tip 32 is a hollow hemispheric structure having a diameter of about 1 inch, a length of about 1 1/2 inch, and has a central aperture 35 on its axis. Typically, aperture 35 has a non-critical diameter of 1/4 to 3/8 inch. In use, the aperture 35 is sealed against the surface to be treated and particles from conduit 30 pass by and abrade the skin exposed through aperture 35. The used sand particles and abraded tissue are then removed through channel 34 and are directed to a novel waste filter 40.

Waste filter 40 is comprised of a cylindrical metal container 41 (FIGS. 2 and 3) which may have a 6 inch diameter and within which is provided a cylindrical filter element 42. This may be formed of a pleated inner portion 42a overwrapped with a flat filter paper layer portion 42b. A standard 3 pound coffee can has been used for container 41. Filter portions 42a and 42b are sized to ensure trapping of the 120 micron sized particles and the abraded tissue. Filter element 42 defines a boundary between a central volume 50a enclosed by the filter and an exterior generally annular shaped sealed volume defined between the filter and the outer container.

Figure 2:
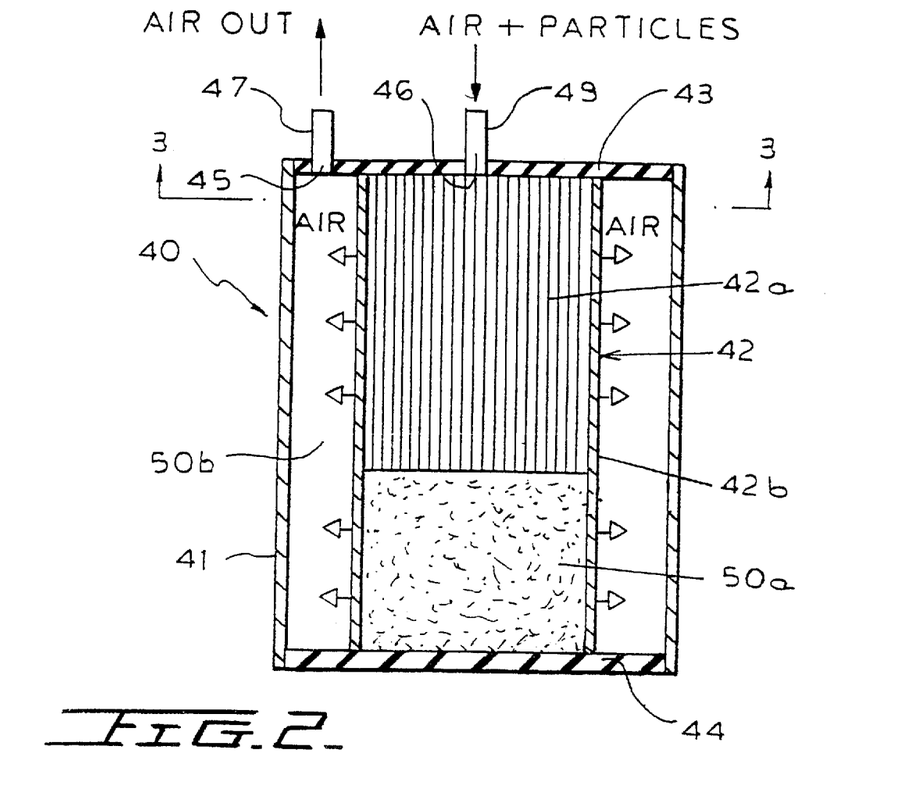
FIG. 2 is a schematic cross-sectional view of the novel filter structure of FIG. 1.

The cylindrical filter element 42 is fixed as by cementing at top and bottom to rubber flange disks 43 and 44 respectively best shown in FIG. 2. These may be formed of a silicone rubber about 1/4 inch thick. The top disk 43 has openings 45 and 46 which receive air outlet conduit 47 and an air-plus-particle inlet conduit 49. Conduits 47 and 49 are fused or otherwise sealingly connected to openings in disk 43. Conduits 47 and 49 may be flexible plastic tubes with O.D.'s of 3/8 and 1/4 inch respectively.

The disks 43 and 44 are press-fitted into the inner diameter of can 41 and can be glued to the can interior. They form the sealed annular chamber 50b which surrounds filter 42 and communicates with conduit 47.

Figure 13:
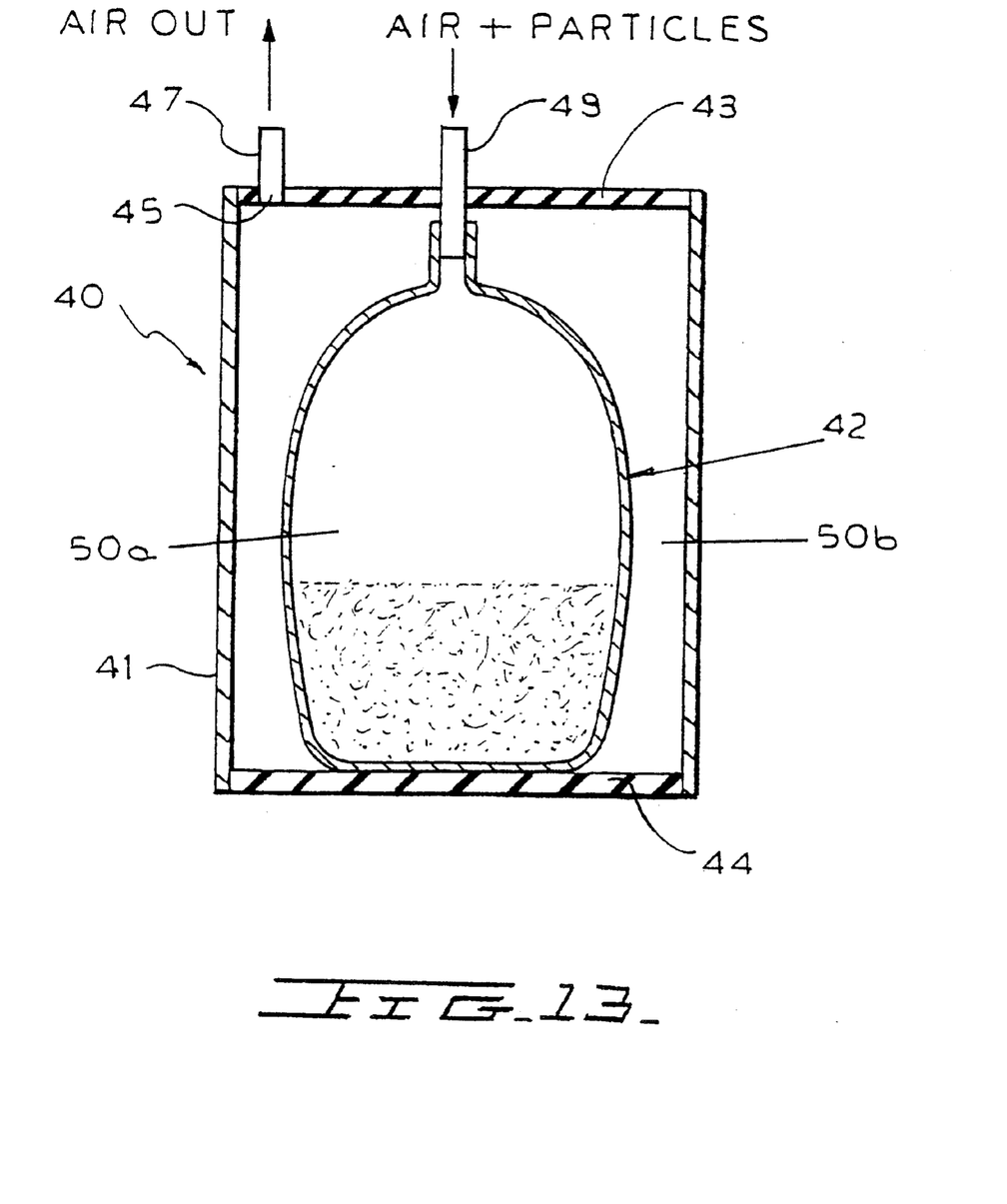
FIG. 13 is a schematic cross-sectional view similar to FIG. 2 showing an alternative construction of the novel filter structure of FIG. 1.

While filter 42 element is shown as a rigid filter fixed between rubber disks 43 and 44, it can be replaced by a simple filter bag suitably clamped to input conduit 49 (see FIG. 13).

In operation, waste particles and tissue flow from the handpiece and into filter 42 element and are collected within central volume 50a. Filtered air passes through the filter element 42 and into the low pressure annular volume 50b and out through conduit 47 toward vacuum pump 60. This filtered air also flows through an emergency back-up filter 55 which prevents flow of abrasive particles into vacuum pump 60 (a 1/3 horse power pump) if filter element 42 is accidentally bypassed. A 3/8 inch conduit 61 connects filter 55 to pump 60.

Since waste filter 40 is formed of components which are permanently secured together to form a unitary structure, it is conveniently removable, and disposable in one piece by disconnection of conduits 47 and 49 respectively from backup filter 55 and output channel 34 in handpiece 31.

A pressure gauge 62 monitors the pressure at the input to pump 60 (reading from 0 to 100KPA vacuum). The exhaust air from pump 60 is exhausted to the exterior atmosphere through muffler 65. A valve 66 controls the vacuum in line 61.

It will be noted that valves 23 and 66 along with selected other elements of the system may be housed in a control box (not shown). The filters 40 and 55 and reservoir 20 are suitably mounted for greatest convenience. The handpiece 31 is connected to the particle supply by the elongated and flexible supply line 22, and to the filter 40 by a similar elongated flexible line 70. Lines 22 and 70 ensure that an operator can manipulate the handpiece 31 as necessary for its use.

Figure 3:
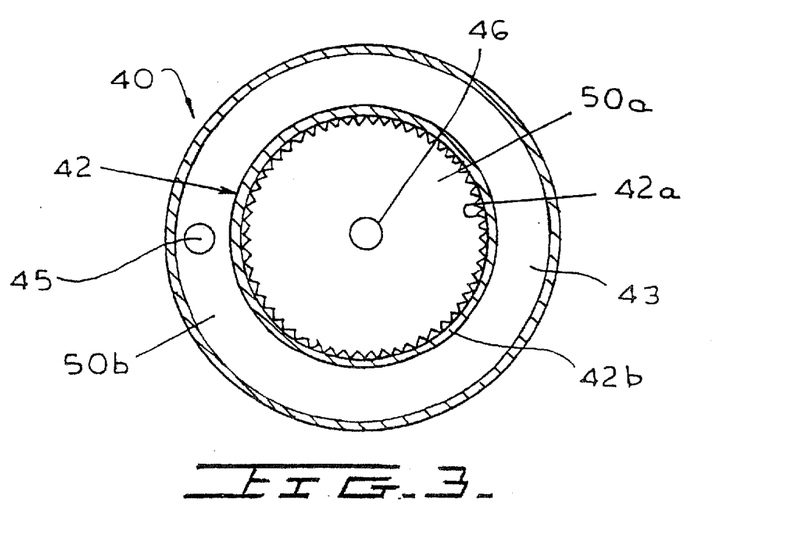
FIG. 3 is a cross-sectional view along line 3—3 in FIG. 2.
Figure 4:
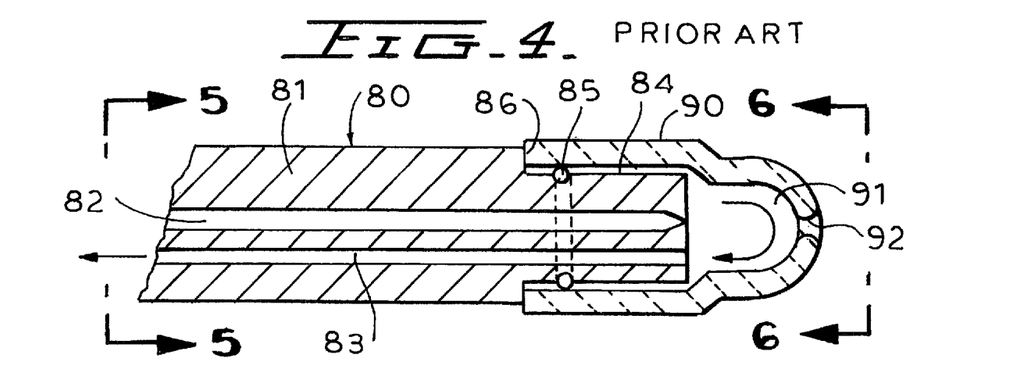
FIG. 4 is a cross-sectional view of a prior art handpiece.
Figure 5:
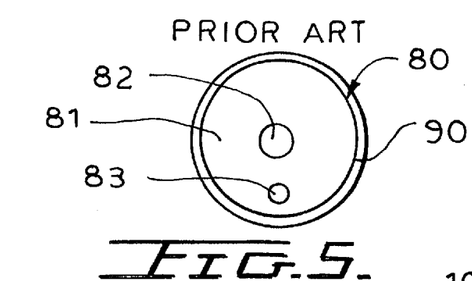
FIG. 5 is a view of the handpiece of FIG. 4 as seen from line 5—5 in FIG. 4.
Figure 6:
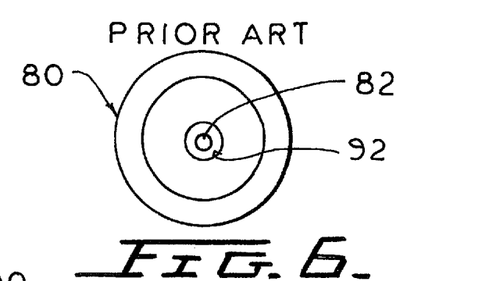
FIG. 6 is a view of the handpiece of FIG. 4 as seen from line 6—6 in FIG. 4.

FIGS. 4, 5 and 6 show a prior art type of handpiece 80 which can be used with the novel filter and system of FIGS. 1, 2 and 3. The handpiece 80 consists of a solid plastic body 81 having a large diameter channel 82 which is coaxial with the axis of body 81 and a smaller diameter outflow channel 83. A restrictive nozzle is commonly placed at the end of channel 82. Body 80 has a length of about 5 inches and a reduced diameter end section 84, about 1 inch long. An O-ring gasket 85 is fixed around the diameter of section 84, at a point removed from the shoulder 86. A rigid transparent plastic tip 90 is pressed over gasket 85 to form a chamber 91 leading to a central hole or aperture 92.

In use, the hole 92 is pressed (or sealed) against the skin area to be treated. Abrading particles flowing along channel 82 and in line and coaxial with hole 92 impinge on the skin exposed through hole 92 and the used particles and abraded skin are reflected from the skin and are withdrawn through channel 83.

Figure 7:
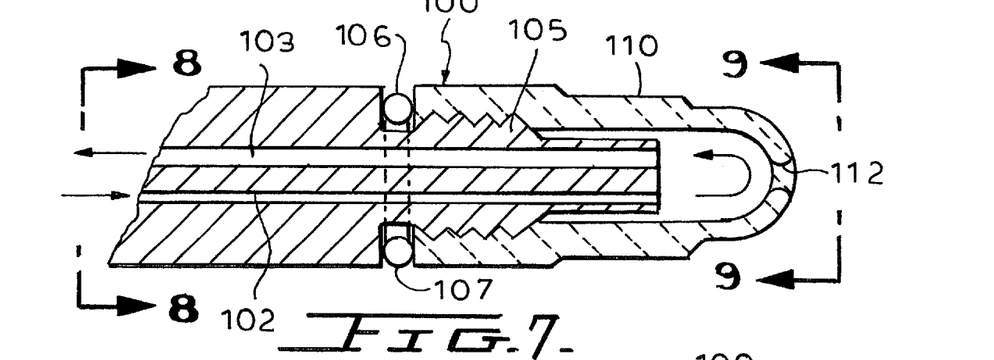
FIG. 7 is a cross-sectional view of a novel handpiece containing many of the features of the present invention.
Figure 8:
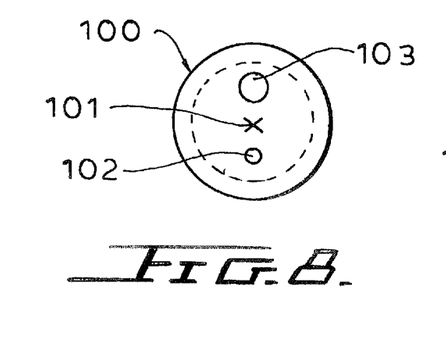
FIG. 8 is a view of the handpiece of FIG. 7 as seen from line 8—8 in FIG. 7.
Figure 9:
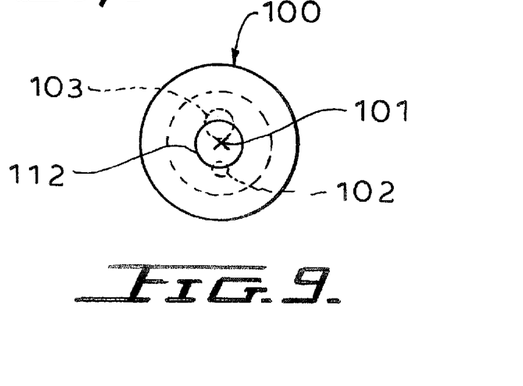
FIG. 9 is a view of FIG. 7 as seen from the line 9—9 in FIG. 7.

FIGS. 7, 8 and 9 show a handpiece modified in accordance with several of the features of the invention. Thus body 100 of rigid plastic, for example Teflon, has a central axis 101 (FIGS. 8 and 9) and off-center inlet and outlet channels 102 and 103 respectively. Note that these channels are reversed in relative sizes from those of FIG. 4 and are 1/8 inch and 1/4 inch respectively.

The body 100 has a very short length, less than about 3 inch and has a reduced diameter threaded end section 105. A sealing O-ring 106 is placed against shoulder 107 between the large diameter and small diameter sections of body 100. A transparent plastic tip 110 is then threaded onto the threaded portion of body extension 105 and compresses O-ring 106 against shoulder 107 to create a seal. The tip 110 forms a vacuum chamber 111 interior spaced from the end of body 100 and has a central aperture 112 (FIGS. 7 and 9) which is about 5/16 inch in diameter and is laterally off-set from the axis of channels 102 and 103.

The novel shortened length of handpiece 100 makes it easier for an operator to manipulate the opening 112 over the skin of a patient. Further the large output diameter of channel 103 improves the operation of the device and makes it easier to quickly evacuate particles from chamber 111 to ensure against loss of particles to atmosphere if the handpiece is removed from the skin of a subject, breaking the vacuum in chamber 111.

As a further advantage over prior handpieces, the tip 110 can be easily detached and replaced by a new tip after use on a given patient by simply unscrewing the tip and screwing on a new one for the next patient. In the prior art structure of FIGS. 4, 5 and 6, the press fit of tip 90 over seal 85 formed a tight fit making it difficult to remove the used tip and replace it with a new one.

Figure 10:
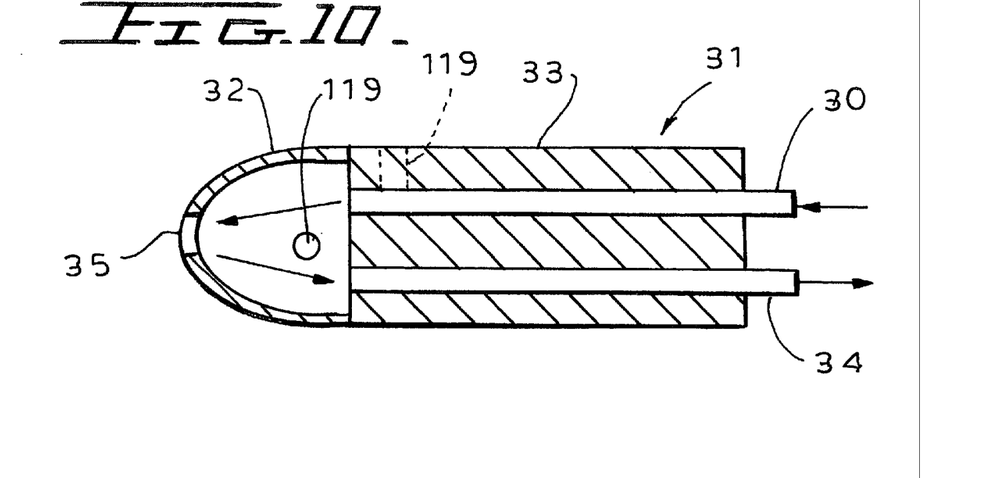
FIG. 10 schematically shows a novel handpiece which contains a sand velocity control aperture in the tool tip.
Figure 11:
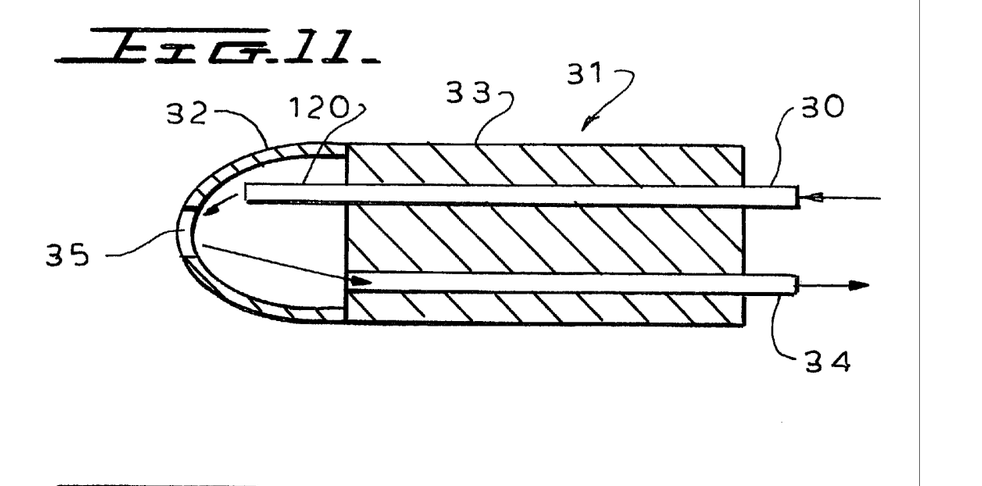
FIG. 11 schematically shows a handpiece which contains an extended sand input channel which extends into the tip interior.
Figure 12:
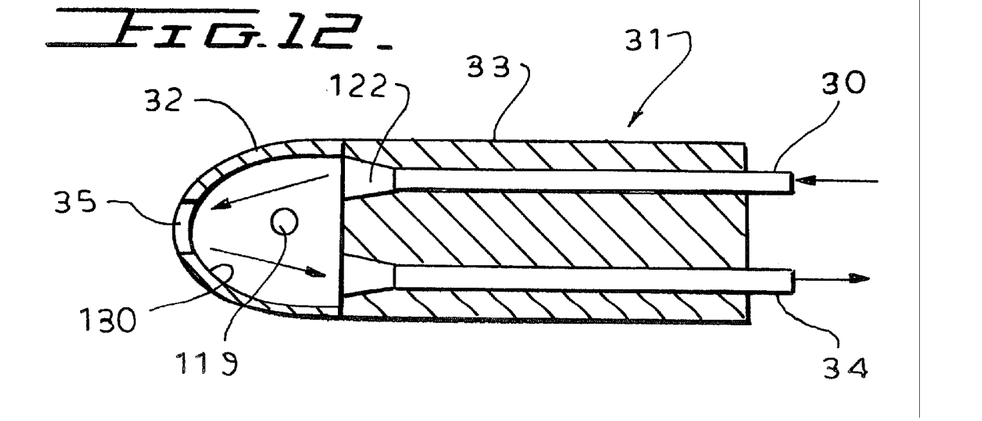
FIG. 12 schematically shows enlarged flares at the ends of the input and output channels in the handpiece to prevent clogging.

FIGS. 10, 11 and 12 schematically show several novel features for handpiece 31 of FIG. 1 which can be used with the handpieces of FIGS. 4 to 9. Thus, in FIG. 10, the tip 31 is shown with a small control opening 119 therein which can be easily closed by the operator's finger to increase the vacuum to produce a more forceful stream of abrasive particles against the skin being abraded when such added force is required. This can be done directly at the handpiece, without requiring the operator to reach for the equipment housing valve 66 in FIG. 1.

It should be further noted that the same result can be obtained by placing the control opening in the body of the handpiece and in communication with either the interior of the tip or the input channel or the output channel.

FIG. 11 shows a modification in which a tube 120 is added to channel 30 in body 33 to extend the point of exit of new abrading particles closer to opening 35 and the skin being treated.

FIG. 12 shows a variation in which the ends of channels 30 and 34 are flared outward at diffuser regions 122 and 123 respectively. It has been found that these diffuser flares tend to prevent clogging of the channels 30 and 34 at their ends entering vacuum chamber 130 formed by tip 31. Note that in prior art handpieces a restriction nozzle has been used at the outlet of channel 30 which has been found to aggravate clogging of the handpiece after a short time.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. Microdermal abrasion apparatus comprising:

a supply container for abrasive particles;

a handpiece for applying an input stream of abrasive particles to a skin surface through a first passage and for withdrawing a waste stream of abrasive particles and abraded tissue from the skin surface through a second passage;

a connection line between the first passage of the handpiece and the supply container to provide the input stream of abrasive particles;

a waste filter that is installable and removable for disposal as a complete unit, the waste filter being comprised of:

an integral outer container;

a filter inlet conduit releasably connected to the second passage in the handpiece;

a filter outlet conduit for an air stream from which the abrasive particles and abraded skin have been filtered; and a filter element positioned within the outer container, and integrally disposable therewith, the filter element defining a boundary between a central volume therein and an exterior sealed volume between the filter element and the outer container; and a vacuum pump having a vacuum line releasably connected to the outlet conduit.

2. The apparatus described in claim 1, further including an air input line connected to the vacuum line and having a vacuum strength control valve therein.

3. The apparatus described in claim 1, further including a secondary filter disposed in the vacuum line.

4. The apparatus described in claim 1, further including an air input line connected from ambient to the connection line and a particle flow control valve connected in the air input line.

5. The apparatus described in claim 4, further including an air input line connected to the vacuum line and having a vacuum strength control valve therein.

6. The apparatus described in claim 1, wherein the outer container includes integral end and body portions, and wherein the Filter element is comprised of a tubular body having inner and outer surfaces, the tubular body extending between the end portions of the outer container, and being sealingly connected thereto, the central volume being defined by the inner surface of the tubular body and the exterior volume being defined by the outer surface of the tubular body and the outer container.

7. The apparatus described in claim 6, wherein the inlet conduit is in communication with the central volume and the outlet conduit is in communication with the exterior sealed volume, and the waste stream is directed substantially axially into the central volume.

8. The apparatus described in claim 7, wherein the inlet conduit is in communication with the central volume and the outlet conduit is in communication with the exterior sealed volume through the same end portion of the outer container.

9. The apparatus described in claim 1, wherein the inlet conduit is in communication with the central volume, the outlet conduit is in communication with the exterior sealed volume, and the central volume provides a receptacle for the abrasive particles and abraded skin filtered from the waste stream.

10. The apparatus described in claim 9, wherein the inlet conduit is in communication with the central volume and the outlet conduit is in communication with the exterior sealed volume through a single end of the outer container.

11. The apparatus described in claim 1, wherein the filter element is comprised of a filter bag sealingly attached to the inlet conduit, and disposable with the outer container.

12. The apparatus described in claim 11, wherein the inlet conduit is in communication with the interior of the filter bag and the outlet conduit is in communication with the sealed volume outside of the filter bag, through the same end portion of the outer container.

13. The apparatus described in claim 1, wherein the filter element is comprised of a rigid tubular body having two open ends sealingly connected to the outer container.

14. The apparatus described in claim 1, wherein the body portion of the outer container is comprised of a tubular body having integral end portions with the filter element positioned therein, and wherein the open ends of the filter element are integrally attached to the end portions of the outer container.

15. The apparatus described in claim 1, wherein the handpiece comprises:

a rigid elongated body member having a central axis and a removable tip at one end thereof;

the removable tip being in communication with the first and second passages in the handpiece and having an outlet opening which is coaxial with the central axis;

the interior of the removable tip defining a vacuum chamber between the end of the rigid elongated body member and the outlet opening therein, when the outlet opening is sealed against the skin to be abraded.

16. The apparatus described in claim 15, wherein the removable tip is connected to the rigid elongated body member by a threaded connection.

17. The apparatus described in claim 15 wherein one of the handpiece and removable tip have a small opening therein in communication with the interior of the removable tip to permit the easy change of the vacuum pressure within the vacuum chamber by an operator during use of the handpiece.

18. The apparatus described in claim 15, wherein the second passage has larger diameter than the first passage.

19. The apparatus described in claim 15, wherein both the first and second passages are laterally displaced from and are on opposite sides of the central axis.

20. The apparatus described in claim 15, wherein the handpiece has a total length less than about 3 inches.

21. A handpiece for a microdermal abrasion apparatus comprising:

a rigid elongated body member having a central axis and a removable tip threadedly connected at one end of the rigid elongated body member;

the removable tip having an outlet opening which is coaxial with the central axis;

the rigid elongated body member having first and second spaced passages therethrough which are respectively connectable to first and second connection lines to respectively conduct a stream of abrasive particles toward the removable tip and to conduct the abrasive particles and abraded skin away from the removable tip, the diameter of the second passage being larger than the diameter than the first passage;

the interior of the removable tip defining a vacuum chamber between the end of the rigid elongated body member and the outlet opening therein when the outlet opening is sealed against the skin to be abraded.

22. The handpiece described in claim 21, wherein the removable tip has a small opening therein to permit the easy change of the vacuum pressure within the vacuum chamber by an operator during use.

23. The handpiece described in claim 21, wherein the first and second passages are parallel to each other and are on opposite sides of the central axis.

24. The apparatus described in claim 23, wherein the handpiece has a total length less than about 3 inches.

25. A method for microdermal abrasion comprising:

producing a steam of abrasive particles from a supply container;

directing the stream of particles through a first passage in a handpiece toward a skin surface;

withdrawing a waste stream of abrasive particles and abraded skin through a second passage in the handpiece;

filtering the waste stream through a waste filter having an integral outer container, and a filter element sealingly contained within the outer container, withdrawing a filtered air stream from the interior of the waste filter; and disposing of the waste filter when necessary without disassembly of the outer container.

26. The method described in claim 25, wherein one of the handpiece and removable tip have a second opening therein which is removed from the first mentioned opening, whereby an operator can change the pressure within the removable tip by manually closing the outlet opening while otherwise manipulating the removable tip over the skin surface.

27. A method as described in claim 25, wherein the filter element defines a boundary between a central volume enclosed therein and an exterior sealed volume between the filter and the outer container.

28. A method as described in claim 27, wherein the waste stream is directed into the central volume, the filtered air stream is withdrawn from the exterior sealed volume of the filter, and the central volume provides a receptacle for the abrasive particles and abraded skin filtered from the waste stream.

29. A method as described in claim 25, wherein power for directing the stream of particles from the supply container through the first passage in the handpiece, for delivering the waste stream to the waste filter and for withdrawing the filtered air stream from the waste filter is provided by a vacuum pump releasably connected to an outlet conduit from the waste filter.

30. A method as described in claim 25, wherein the filter element is comprised of a tubular body having open ends sealably attached to the outer container.

31. A method as described in claim 30, wherein the outer container of the waste filter is a cylindrical tube having integral ends to which the open ends of the filter element are sealingly attached.

32. A method as described in claim 25, wherein the filter element is comprised of an open ended tubular body having inner and outer surfaces, the tubular body being sealingly connected at its open ends to the outer container, the central volume being defined by the inner surface of the tubular body and the exterior volume being defined by the outer surface of the tubular body and the outer container.

33. A method as described in claim 32, wherein the inlet conduit is in communication with the central volume, the outlet conduit is in communication with the exterior sealed volume, and the central volume provides a receptacle for the particles and abraded skin filtered from the waste stream.

34. A method as described in claim 33, wherein the inlet conduit is in communication with the central volume and the outlet conduit is in communication with the exterior sealed volume through a single end of the outer container.

35. A method as described in claim 25, wherein the filter element is comprised of a filter bag sealingly attached to the inlet conduit, and disposable with the outer container as a complete unit.

* * * * *